United States Patent [19]

Kawai et al.

[11] Patent Number: 4,814,320

[45] Date of Patent: Mar. 21, 1989

[54] HEAT-SENSITIVE RECORDING MATERIAL

[75] Inventors: Hajime Kawai, Tsuzuki; Masatoshi Taniguchi; Katsuhiko Tsunemitsu, both of Kyoto, all of Japan

[73] Assignee: Yamada Chemical Co., Ltd., Kyoto, Japan

[21] Appl. No.: 59,525

[22] Filed: Jun. 8, 1987

Related U.S. Application Data

[63] Continuation-in-part of Ser. No. 37,669, Apr. 13, 1987, and a continuation-in-part of Ser. No. 37,665, Apr. 13, 1987.

[30] Foreign Application Priority Data

Apr. 15, 1986 [JP] Japan ................................ 61-87619
Apr. 16, 1986 [JP] Japan ................................ 61-88961
May 1, 1986 [JP] Japan ................................ 61-102909
Jun. 9, 1986 [JP] Japan ................................ 61-134072
Feb. 2, 1987 [JP] Japan ................................ 62-23361

[51] Int. Cl.$^4$ ........................................... B41M 5/22
[52] U.S. Cl. ................................... 503/220; 427/151; 428/913; 428/914; 503/221; 503/223; 503/224
[58] Field of Search ........................ 427/150–152; 503/218, 220, 221, 223, 224, 225; 428/913, 914

[56] References Cited

U.S. PATENT DOCUMENTS

| | | | |
|---|---|---|---|
| 4,020,056 | 4/1977 | Farber | 503/220 |
| 4,022,771 | 5/1977 | Farber | 503/220 |
| 4,107,428 | 8/1978 | Farber | 503/220 |
| 4,119,776 | 10/1978 | Farber | 503/220 |
| 4,580,153 | 4/1986 | Kondo et al. | 503/220 |

FOREIGN PATENT DOCUMENTS

| | | | |
|---|---|---|---|
| 0062544 | 10/1982 | European Pat. Off. | 503/220 |
| 0127203 | 12/1984 | European Pat. Off. | 503/220 |
| 0188377 | 7/1986 | European Pat. Off. | 503/220 |
| 242169A2 | 12/1987 | European Pat. Off. | 503/220 |
| 242170A2 | 6/1988 | European Pat. Off. | 503/220 |
| 60-8364 | 1/1985 | Japan | 503/204 |

*Primary Examiner*—Bruce H. Hess
*Attorney, Agent, or Firm*—Nixon & Vanderhye

[57] ABSTRACT

Disclosed herein is a heat-sensitive recording material in which a chromogenic dye-procursor comprises:

(A) a mixture comprising at least two divinyl phthalide compounds represented by the formula (I):

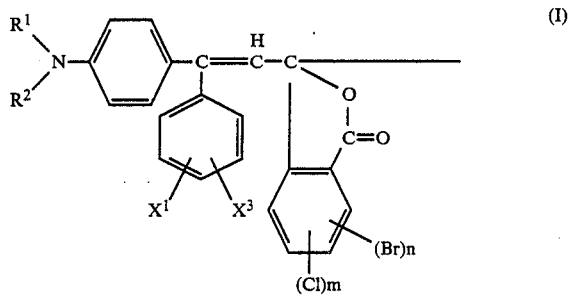

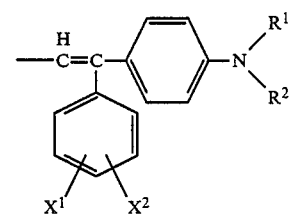

wherein $R^1$ and $R^2$ represent respectively alkyl group of 1 to 6 carbon atoms, alkyl group of 1 to 4 carbon atoms having an alkoxy group of 1 to 4 carbon atoms or cycloalkyl group of 5 to 7 carbon atoms, $X^1$ and $X^2$ represent respectively hydrogen atom, alkyl group of 1 to 8 carbon atoms, alkoxy group of 1 to 8 carbon atoms, alkoxy group of 1 to 4 carbon atoms having an alkoxy group of 1 to 4 carbon atoms, cycloalkoxy group of 5 to 7 carbon atoms, alkenyloxy group of 3 to 8 carbon atoms, benzyloxy group, substituted benzyloxy group, furfurloxy group, tetrahydrofurfuryloxy group, phenyl group, substituted phenyl group, phenoxy group, substituted phenoxy group, fluorine atom, chlorine atom or bromine atom, m and n represent 0 or integer of 1 to 4, m+n=4 and $R^1$ and $R^2$ may join together to form a heterocyclic ring, or (B) a mixture of the divinyl phthalide compound(s) represented by the formula (I) and at least one compound selected from the compounds represented by the formulas (II), (III) and (IV):

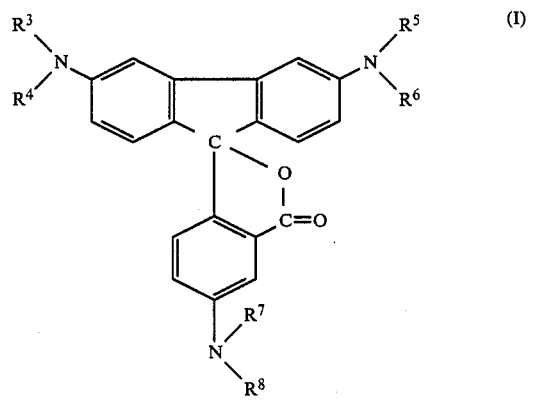

(Abstract continued on next page.)

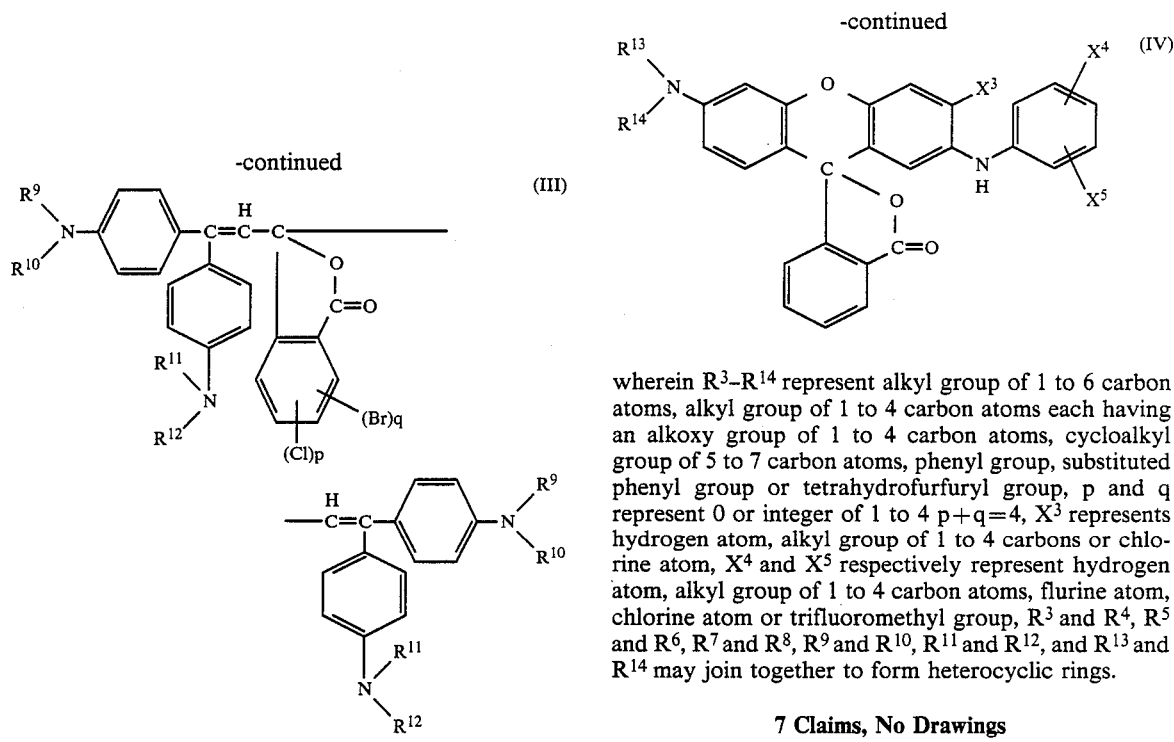

wherein $R^3$–$R^{14}$ represent alkyl group of 1 to 6 carbon atoms, alkyl group of 1 to 4 carbon atoms each having an alkoxy group of 1 to 4 carbon atoms, cycloalkyl group of 5 to 7 carbon atoms, phenyl group, substituted phenyl group or tetrahydrofurfuryl group, p and q represent 0 or integer of 1 to 4 p+q=4, $X^3$ represents hydrogen atom, alkyl group of 1 to 4 carbons or chlorine atom, $X^4$ and $X^5$ respectively represent hydrogen atom, alkyl group of 1 to 4 carbon atoms, flurine atom, chlorine atom or trifluoromethyl group, $R^3$ and $R^4$, $R^5$ and $R^6$, $R^7$ and $R^8$, $R^9$ and $R^{10}$, $R^{11}$ and $R^{12}$, and $R^{13}$ and $R^{14}$ may join together to form heterocyclic rings.

7 Claims, No Drawings

HEAT-SENSITIVE RECORDING MATERIAL

CROSS-REFERENCE TO RELATED APPLICATION

The present application is a continuation-in-part of application Ser. No. 037,669, filed Apr. 13, 1987 and application Ser. No. 037,665, filed Apr. 13, 1987.

BACKGROUND OF THE INVENTION

The present invention relates to a heat-sensitive recording material wherein a developed black color image shows absorption in the near infrared region and is excellent in moisture resistance, resistance to plasticizer, oil resistance and light fastness. More specifically, the present invention relates to a heat-sensitive recording material comprising, as a chromogenic dye-precursor, (A) a mixture comprising at least two divinyl phthalide compounds represented by the formula (I):

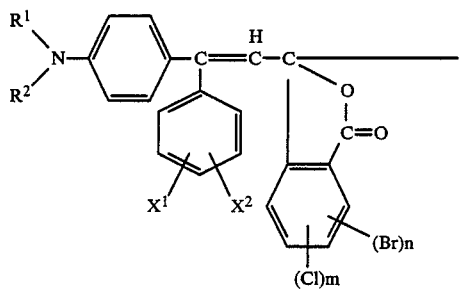

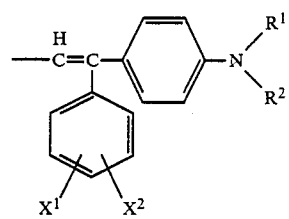

wherein $R^1$, $R^2$ represent respectively alkyl group of 1 to 6 carbon atoms, alkyl group of 1 to 4 carbon atoms having alkoxy group of 1 to 4 carbon atoms or cycloalkyl group of 5 to 7 carbon atoms, $X^1$, $X^2$ represent respectively hydrogen atom, alkyl group of 1 to 8 carbon atoms, alkoxy group of 1 to 8 carbon atoms, alkoxy group of 1 to 4 carbon atoms having alkoxy group of 1 to 4 carbon atoms, cycloalkoxy group of 5 to 7 carbon atoms, alkenyloxy group of 3 to 8 carbon atoms, benzyloxy group, substituted benzyloxy group, furfuryloxy group, tetrahydrofurfuryloxy group, phenyl group, substituted phenyl group, phenoxy group, substituted phenoxy group, fluorine atom, chlorine atom or bromine atom, and m and n represent 0 or integer of 1 to 4, n+m=4 and $R^1$ and $R^2$ may join together to form a heterocyclic ring, or (B) a mixture of the divinyl phthalide compound(s) represented by the formula (I) and at least one compound selected from the compounds represented by the formulas (II), (III) and (IV).

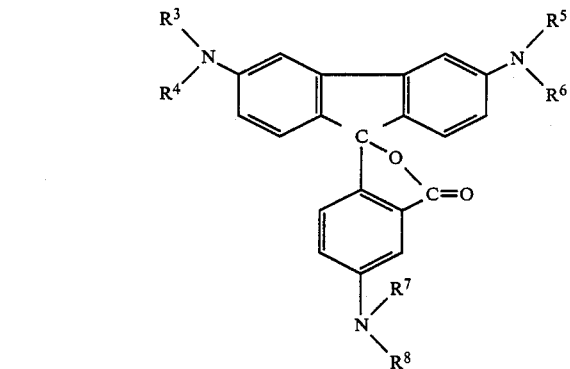

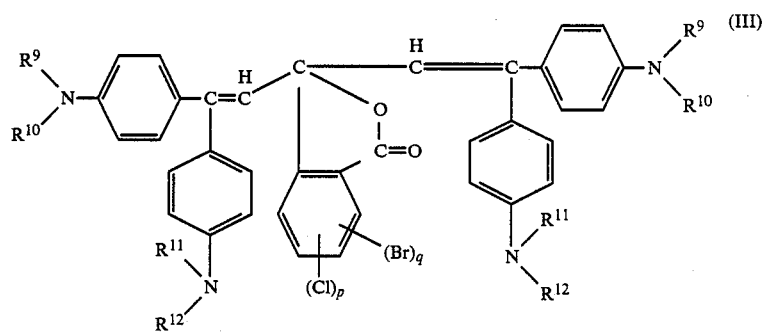

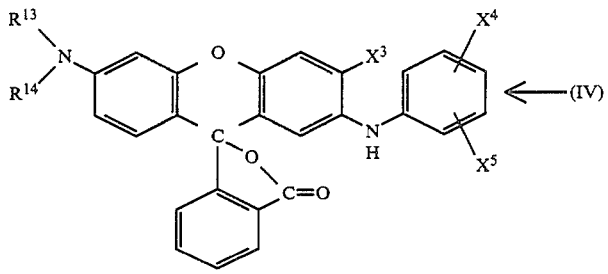

wherein $R^3$–$R^{14}$ represent alkyl group of 1 to 6 carbon atoms, alkyl group of 1 to 4 carbon atoms having alkoxy group of 1 to 4 carbon atoms, cycloalkyl group of 5 to 7 carbon atoms, phenyl group, substituted phenyl group or tetrahydrofurfuryl group, p and q represent 0 or integer of 1 to 4, p+q=4 and $X^3$ represents hydrogen atom, alkyl group of 1 to 4 carbon atoms or chlorine atom, $X^4$, $X^5$ represent hydrogen atom, alkyl group of 1 to 4 carbon atoms, chlorine atoms, fluorine atom or trifluoromethyl group, and each of $R^3$ and $R^4$, $R^5$ and $R^6$, $R^7$ and $R^8$, $R^9$ and $R^{10}$, $R^{11}$ and $R^{12}$, and $R^{13}$ and $R^{14}$ may join together to form a heterocyclic ring.

Heat-sensitive recording paper sheets using so-called leuco dyes have generally been used as recording paper for facsimiles and various printers, POS (point of sales) labels, railway tickets, etc. and the demands for the same have increased rapidly, since they have the appearance of ordinary paper, require no fixing because of primary color development and enable high speed recording with no noises, and the devices using them are small in the size, reduced in the weight, inexpensive and are free from maintainance work.

It is important for such heat-sensitive recording paper sheet that it is free from background coloration and excellent in color development sensitivity, color development density, and light fastness and storage stability (moisture resistance, resistance to plasticizer, oil resistance, etc.) of developed color image. It is also important that a heat-sensitive recording paper wherein developed color image shows absorption at the near infrared region has the same properties as above, but no satisfactory material has yet been obtained at present.

For improving the light fastness and the storage stability of the developed color image, it has been known to use of a mixture of two or more of chromogenic dye-precursors as described, for example, in Japanese Patent Publication No. 59-53193 (1984) (U.S. Pat. No. 4226912), Japanese patent application laying-open (KOKAI) Nos. 56-105990 (1981), 57-123085 (1982), 58-71192 (1983), 58-119892 (1983) and 61-76387 (1986). However, any mixture disclosed in these publications is prepared by mixing fluoran compounds with each other and thus it cannot always be said that the light fastness and the storage stability of developed color images are excellent.

The present inventors have made an earnest study for improving the foregoing drawbacks and, as a result, it have been found that the storage stability of the developed color image can be improved and the color developing sensitivity and the light fastness of the image can also be improved unexpectedly when a mixture prepared by mixing at least two divinyl phthalide compounds of the formula (I) or mixing the divinyl phthalide compound(s) of the formula (I) with at least one compound selected from the compounds represented by the formulas (II), (III) and (IV) is used as a chromogenic dye-precursor, and based on this findings, the present invention has been accomplished.

SUMMARY OF THE INVENTION

In an aspect of the present invention, there is provided a heat-sensitive recording material in which a chromogenic dye-precursor comprises:

(A) a mixture comprising at least two divinyl phthalide compounds represented by the formula (I):

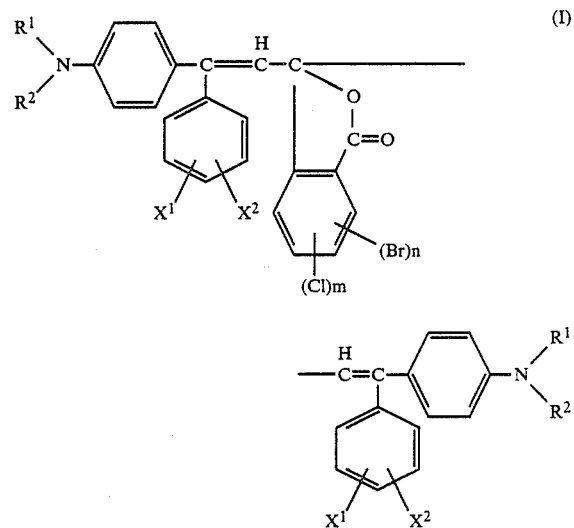

wherein $R^1$ and $R^2$ represent respectively alkyl group of 1 to 6 carbon atoms, alkyl group of 1 to 4 carbon atoms having an alkoxy group of 1 to 4 carbon atoms or cycloalkyl group of 5 to 7 carbon atoms, $X^1$ and $X^2$ represent respectively hydrogen atom, alkyl group of 1 to 8 carbon atoms, alkoxy group of 1 to 8 carbon atoms, alkoxy group of 1 to 4 carbon atoms having an alkoxy group of 1 to 4 carbon atoms, cycloalkoxy group of 5 to 7 carbon atoms, alkenyloxy group of 3 to 8 carbon atoms, benzyloxy group, substituted benzyloxy group, furfuryloxy group, tetrahydrofurfuryloxy group, phenyl group, substituted phenyl group, phenoxy group, substituted phenoxy group, fluorine atom, chlorine atom or bromine atom, m and n represent 0 or integer of 1 to 4, m+n=4 and $R^1$ and $R^2$ may join together to form a heterocyclic ring, or (B) a mixture of the divinyl phthalide compound(s) represented by the formula (I) and at least one compound selected from the compounds represented by the formulas (II), (III) and (IV):

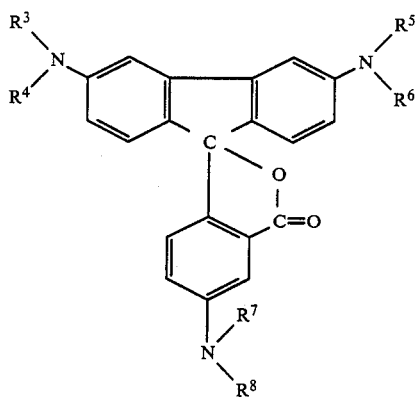

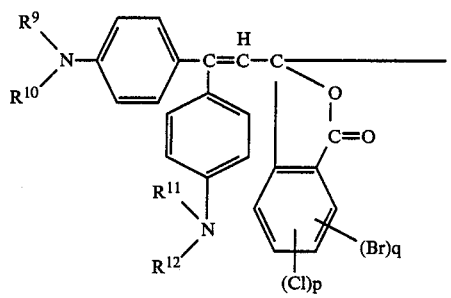

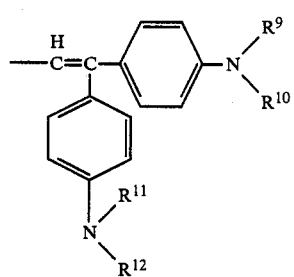

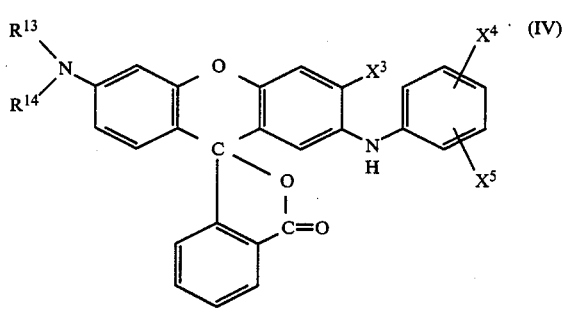

wherein $R^3$–$R^{14}$ represent alkyl group of 1 to 6 carbon atoms, alkyl group of 1 to 4 carbon atoms each having an alkoxy group of 1 to 4 carbon atoms, cycloalkyl group of 5 to 7 carbon atoms, phenyl group, substituted phenyl group or tetrahydrofurfuryl group, p and q represent 0 or integer of 1 to 4, p+q=4, $X^3$ represents hydrogen atom, alkyl group of 1 to 4 carbon atoms or chlorine atom, $X^4$ and $X^5$ respectively represent hydrogen atom, alkyl group of 1 to 4 carbon atoms, fluorine atom, chlorine atom or trifluoromethyl group, $R^3$ and $R^4$, $R^5$ and $R^6$, $R^7$ and $R^8$, $R^9$ and $R^{10}$, $R^{11}$ and $R^{12}$, and $R^{13}$ and $R^{14}$ may join together to form heterocyclic rings.

DETAILED DESCRIPTION OF THE INVENTION

Divinyl phthalide compounds of the formula (I) are described in Japanese patent application Nos. 61-87619, 61-88961 and 61-102909 (corresponding to U.S. patent applications No. (unknown) filed Apr. 13, 1987 and No. (unknown) filed Apr. 13, 1987), which are substantially colorless by themselves, extremely stable in an atmospheric air, free from sublimation and spontaneous color development (background fogging), and are highly soluble to an organic solvent. In addition, they are rapidly converted to black-colored substances by developer and form developed color image excellent in the light fastness. Further, since the developed color images show intense absorption at 700–1000 nm in addition to the visible region, they have an advantageous feature of enabling reading by an optical character reader (OCR, OMR) and a bar code reader using near infrared rays.

Further, the compounds of the formula (II) are disclosed in European Patent No. 0124377A2 and the compounds of the formula (III) are disclosed in U.S. Pat. No. 4,020,056 and No. 4,107,428. These compounds are chromogenic dye-precursor and the developed color images formed therefrom show an absorption in the near infrared region. The compounds of the formula (IV) are disclosed in U.S. Pat. No. 3,669,711, No. 3,681,390, No. 3,920,510, No. 3,925,457, No. 3,959,571 and No. 4,444,591, and these compounds are fluoran compounds which may be converted to green or black substances showing no absorption in the near infrared region, and have an effect of improving the storage stability, developed color tone, developed color density and light fastness of the developed color image.

The heat-sensitive recording material can include, for example, heat-sensitive recording paper, electrically heated heat-sensitive recording paper, transfer reaction type heat-sensitive recording paper, etc. using paper, synthetic paper or plastic film as the base.

Specific examples of the compounds of the formulas (I)–(IV) used in the present invention will be described below but the compound is no way limited only thereto.

1. Compound represented by the formula (I):

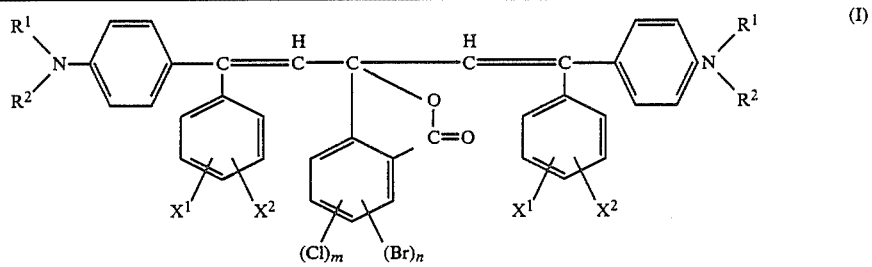

| Compound No. | $R^1R^2N-$ | $X^1$ | $X^2$ | m n | Developed color by bisphenol A |
|---|---|---|---|---|---|
| 1 | $(CH_3)_2N-$ | H | H | m = 4, n = 0 | reddish black |
| 2 | $(CH_3)_2N-$ | H | p-$CH_3$ | m = 4, n = 0 | reddish black |
| 3 | $(CH_3)_2N-$ | H | p-$OCH_3$ | m = 4, n = 0 | black |
| 4 | $(CH_3)_2N-$ | m-$OCH_3$ | p-$OCH_3$ | m = 4, n = 0 | black |
| 5 | $(CH_3)_2N-$ | H | p-$OCH_3$ | m = 0, n = 4 | black |
| 6 | $(CH_3)_2N-$ | H | p-$OCH_3$ | m = 1 (5-Cl), n = 3 | black |
| 7 | $(CH_3)_2N-$ | H | p-$OC_2H_5$ | m = 4, n = 0 | black |
| 8 | $(C_2H_5)_2N-$ | H | p-$OCH_3$ | m = 4, n = 0 | black |
| 9 | $CH_3(i-C_4H_9)N-$ | H | p-$OCH_3$ | m = 4, n = 0 | black |
| 10 | pyrrolidino-N- | p-$CH_3$ | H | m = 4, n = 0 | reddish black |
| 11 | pyrrolidino-N- | H | p-$OCH_3$ | m = 4, n = 0 | black |

-continued

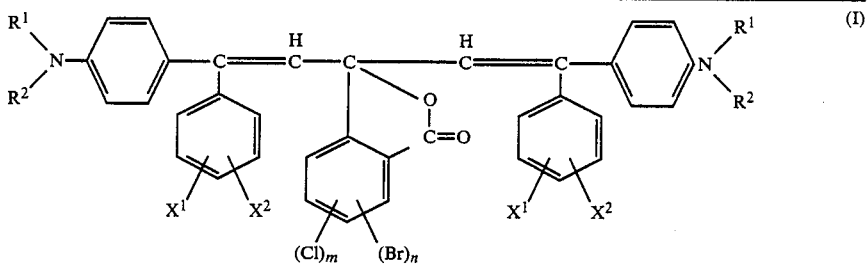

| Compound No. | $\overset{R^1}{\underset{R^2}{>}}N-$ | $X^1$ | $X^2$ | m n | Developed color by bisphenol A |
|---|---|---|---|---|---|
| 12 | 2,6-dimethylpiperidino (CH₃, CH₃ on pyrrolidine/piperidine N) | H | p-OCH₃ | m = 4, n = 0 | black |
| 13 | piperidino | H | p-OCH₃ | m = 4, n = 0 | black |
| 14 | hexamethyleneimino (7-membered) | H | p-CH₃ | m = 4, n = 0 | reddish black |
| 15 | hexamethyleneimino | H | p-OCH₃ | m = 4, n = 0 | black |
| 16 | CH₃, CH₃OC₂H₄–N– | H | p-OCH₃ | m = 4, n = 0 | black |
| 17 | cyclohexyl(CH₃)N– | H | p-OCH₃ | m = 4, n = 0 | black |
| 18 | (CH₃)₂N– | H | p-OC₃H₇ | m = 4, n = 0 | black |
| 19 | (CH₃)₂N– | H | p-O—iso-C₄H₉ | m = 4, n = 0 | black |
| 20 | (CH₃)₂N– | H | p-OC₅H₁₁ | m = 4, n = 0 | black |
| 21 | (CH₃)₂N– | H | p-OC₂H₄OCH₃ | m = 4, n = 0 | black |

-continued

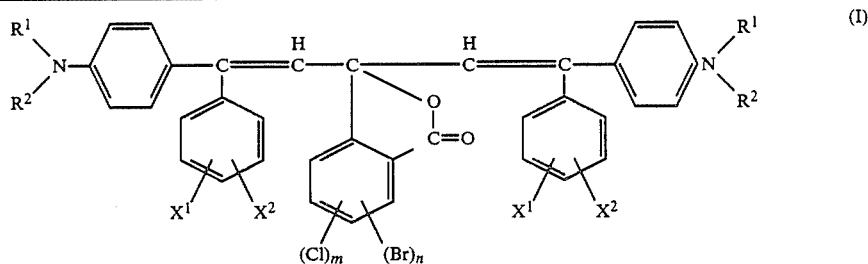

| Compound No. | $\underset{R^2}{\overset{R^1}{\diagdown}}N-$ | $X^1$ | $X^2$ | m n | Developed color by bisphenol A |
|---|---|---|---|---|---|
| 22 | $\underset{CH_3}{\overset{CH_3}{\diagdown}}N-$ | p-O—cyclohexyl | H | m = 4, n = 0 | black |
| 23 | $\underset{CH_3}{\overset{CH_3}{\diagdown}}N-$ | H | p-O—CH$_2$—CH=CH$_2$ | m = 4, n = 0 | black |
| 24 | $\underset{CH_3}{\overset{CH_3}{\diagdown}}N-$ | H | p-O—CH$_2$—phenyl | m = 4, n = 0 | black |
| 25 | pyrrolidin-N— | H | p-O—iso-C$_3$H$_7$ | m = 4, n = 0 | black |
| 26 | pyrrolidin-N— | H | p-OC$_4$H$_9$ | m = 4, n = 0 | black |
| 27 | pyrrolidin-N— | H | p-O—CH$_2$—CH=CH$_2$ | m = 4, n = 0 | black |
| 28 | pyrrolidin-N— | H | p-O—CH$_2$—phenyl | m = 4, n = 0 | black |
| 29 | pyrrolidin-N— | p-O—cyclohexyl | H | m = 4, n = 0 | black |
| 30 | pyrrolidin-N— | p-phenyl | H | m = 4, n = 0 | reddish black |
| 31 | pyrrolidin-N— | p-O—CH$_2$—(2,5-dihydrofuranyl) | H | m = 4, n = 0 | black |

-continued

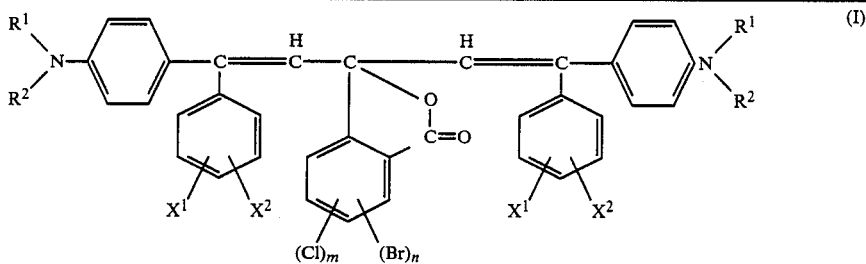

| Compound No. | $\begin{array}{c}R^1\\ \diagdown\\ N-\\ \diagup\\ R^2\end{array}$ | $X^1$ | $X^2$ | m n | Developed color by bisphenol A |
|---|---|---|---|---|---|
| 32 | ![pyrrolidine]N— | p-O-phenyl | H | m = 4, n = 0 | black |
| 33 | ![pyrrolidine]N— | p-O-C₆H₄-OCH₃ | H | m = 4, n = 0 | black |

2. Compound represented by the formula (II):

[Structure II: fluorane with R³R⁴N–, R⁵R⁶N–, R⁷R⁸N– substituents]

| Compound No. | $\begin{array}{c}R^3\\ \diagdown\\ N-\\ \diagup\\ R^4\end{array}$ | $\begin{array}{c}R^5\\ \diagdown\\ N-\\ \diagup\\ R^6\end{array}$ | $\begin{array}{c}R^7\\ \diagdown\\ N-\\ \diagup\\ R^8\end{array}$ | Developed color by bisphenol A |
|---|---|---|---|---|
| 34 | $(CH_3)_2N-$ | $(CH_3)_2N-$ | $(CH_3)_2N-$ | greenish blue |
| 35 | $(CH_3)_2N-$ | $(CH_3)_2N-$ | $(C_2H_5)_2N-$ | greenish blue |
| 36 | $(CH_3)_2N-$ | $(CH_3)_2N-$ | $(C_3H_7)_2N-$ | greenish blue |
| 37 | $(CH_3)_2N-$ | $(CH_3)_2N-$ | pyrrolidin-1-yl | greenish blue |

-continued

| Compound No. | $\underset{R^4}{\overset{R^3}{\diagdown}}\!\!N\!\!-\!$ | $\underset{R^6}{\overset{R^5}{\diagdown}}\!\!N\!\!-\!$ | $\underset{R^8}{\overset{R^7}{\diagdown}}\!\!N\!\!-\!$ | Developed color by bisphenol A |
|---|---|---|---|---|
| 38 | $(C_2H_5)_2N-$ | $(CH_3)_2N-$ | $(CH_3)_2N-$ | greenish blue |
| 39 | $(C_2H_5)_2N-$ | $(C_2H_5)_2N-$ | $(CH_3)_2N-$ | greenish blue |
| 40 | pyrrolidino-N- | $(CH_3)_2N-$ | $(CH_3)_2N-$ | greenish blue |
| 41 | $CH_3(CH_3OC_2H_4)N-$ | $(CH_3)_2N-$ | $(CH_3)_2N-$ | greenish blue |
| 42 | cyclohexyl(CH_3)N- | $(CH_3)_2N-$ | $(CH_3)_2N-$ | greenish blue |

3. Compound represented by the formula (III):

| Compound No. | $\underset{R^{10}}{\overset{R^9}{\diagdown}}\!\!N\!\!-\!$ | $\underset{R^{12}}{\overset{R^{11}}{\diagdown}}\!\!N\!\!-\!$ | p q | Developed color by bisphenol A |
|---|---|---|---|---|
| 43 | $(CH_3)_2N-$ | $(CH_3)_2N-$ | p = 4, q = 0 | green |

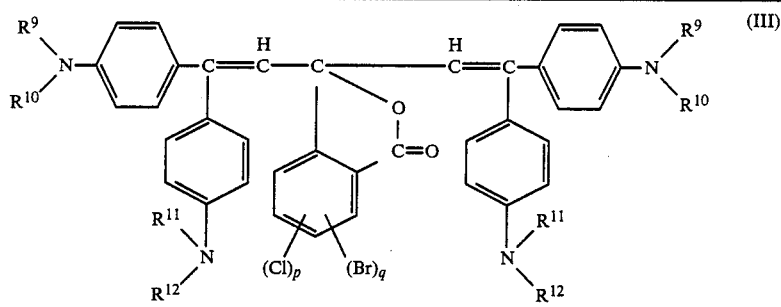

(III)

| Compound No. | $\underset{R^{10}}{\overset{R^9}{N-}}$ | $\underset{R^{12}}{\overset{R^{11}}{N-}}$ | p<br>q | Developed color by bisphenol A |
|---|---|---|---|---|
| 44 | " | " | p = 0<br>q = 4 | " |
| 45 | " | " | p = 1<br>(5-Cl)<br>q = 3 | " |
| 46 | " | " | p = 2<br>(5.6-Cl$_2$)<br>q = 2 | " |
| 47 | $\underset{C_2H_5}{\overset{C_2H_5}{N-}}$ | $\underset{C_2H_5}{\overset{C_2H_5}{N-}}$ | p = 4<br>q = 0 | " |
| 48 | $\underset{CH_3}{\overset{CH_3OC_2H_4}{N-}}$ | $\underset{CH_3}{\overset{CH_3}{N-}}$ | p = 4<br>q = 0 | " |
| 49 | $\underset{CH_3}{\overset{CH_3OC_2H_4}{N-}}$ | $\underset{CH_3}{\overset{CH_3OC_2H_4}{N-}}$ | p = 4<br>q = 0 | " |
| 50 | pyrrolidin-1-yl | $\underset{CH_3}{\overset{CH_3}{N-}}$ | p = 4<br>q = 0 | " |
| 51 | " | pyrrolidin-1-yl | p = 4<br>q = 0 | " |
| 52 | " | " | p = 0<br>q = 4 | " |
| 53 | piperidin-1-yl | $\underset{CH_3}{\overset{CH_3}{N-}}$ | p = 4<br>q = 0 | " |
| 54 | $\underset{H}{\overset{CH_3}{\underset{\text{(cyclohexyl)}}{N-}}}$ | " | p = 4<br>q = 0 | " |

4. Compound represented by the formula (IV):

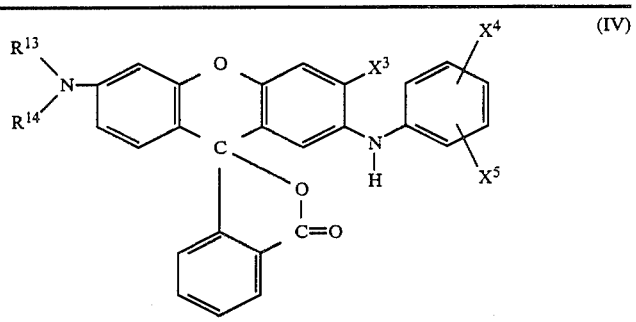

(IV)

| Compound No. | $\underset{R^{14}}{\overset{R^{13}}{\diagdown}} N-$ | $X^3$ | $X^4$ | $X^5$ | Developed color by bisphenol A |
|---|---|---|---|---|---|
| 55 | $\underset{C_2H_5}{\overset{C_2H_5}{\diagdown}} N-$ | H | H | H | greenish black |
| 56 | " | " | " | p-$CH_3$ | " |
| 57 | $\underset{C_4H_9}{\overset{C_2H_5}{\diagdown}} N-$ | " | " | H | " |
| 58 | $\underset{i-C_5H_{11}}{\overset{C_2H_5}{\diagdown}} N-$ | " | " | " | " |
| 59 | $\underset{C_6H_{13}}{\overset{C_2H_5}{\diagdown}} N-$ | " | " | " | " |
| 60 | $\underset{C_2H_5}{\overset{C_2H_5}{\diagdown}} N-$ | $CH_3$ | " | " | black |
| 61 | " | H | o-Cl | " | " |
| 62 | " | " | H | m-$CF_3$ | greenish black |
| 63 | " | Cl | " | H | " |
| 64 | $\underset{C_3H_7}{\overset{CH_3}{\diagdown}} N-$ | $CH_3$ | " | " | black |
| 65 | $\underset{i-C_5H_{11}}{\overset{C_2H_5}{\diagdown}} N-$ | $CH_3$ | H | H | black |
| 66 | $\underset{C_6H_{13}}{\overset{C_2H_5}{\diagdown}} N-$ | " | " | " | " |
| 67 | $\underset{C_4H_9}{\overset{C_4H_9}{\diagdown}} N-$ | " | " | " | " |
| 68 | " | H | " | o-Cl | " |

-continued $$\text{(IV)}$$

Structure (IV): A fluoran-type compound with $R^{13}R^{14}N-$ group on one aromatic ring, an $-NH-$ linked phenyl ring bearing $X^4$ and $X^5$ substituents, $X^3$ on the central ring, and a lactone (phthalide) moiety.

| Compound No. | $\begin{array}{c}R^{13}\\ \diagdown N-\\ R^{14}\end{array}$ | $X^3$ | $X^4$ | $X^5$ | Developed color by bisphenol A |
|---|---|---|---|---|---|
| 69 | $C_2H_5$, $i-C_5H_{11}$ (N-) | $CH_3$ | $o-CH_3$ | $m-CH_3$ | " |
| 70 | $C_2H_5$, $C_2H_5OC_3H_6$ (N-) | " | H | H | " |
| 71 | cyclohexyl-N(CH$_3$)- (H, CH$_3$) | " | " | " | " |
| 72 | tetrahydrofurfuryl-CH$_2$-N(C$_2$H$_5$)- | " | " | " | " |
| 73 | $CH_3$-C$_6$H$_4$-N(C$_2$H$_5$)- | " | " | " | " |
| 74 | pyrrolidin-1-yl | " | " | " | " |
| 75 | piperidin-1-yl | " | " | " | " |
| 76 | hexamethyleneimin-1-yl | " | " | " | " |
| 77 | $C_2H_5$, $C_2H_5$ (N-) | H | o-F | H | greenish black |
| 78 | $C_4H_9$, $C_4H_9$ (N-) | " | " | " | " |

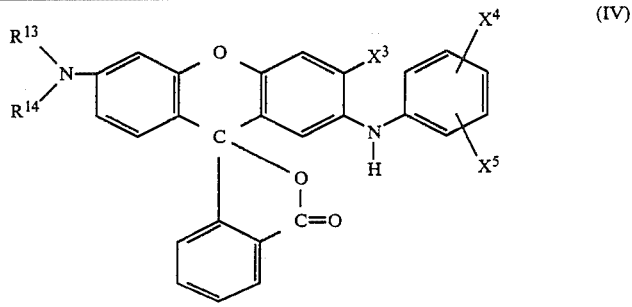

| Compound No. | R¹³ \ N— / R¹⁴ | X³ | X⁴ | X⁵ | Developed color by bisphenol A |
|---|---|---|---|---|---|
| 79 | C₂H₅ \ N— / i-C₅H₁₁ | " | o-Cl | " | black |
| 80 | C₂H₅ \ N— / C₆H₁₃ | " | " | " | " |
| 81 | C₂H₅ \ N— / CH₃OC₃H₆ | CH₃ | H | H | " |
| 82 | CH₃ \ N— / C₂H₅OC₃H₆ | " | " | " | " |
| 83 | C₃H₇ \ N— / C₃H₇ | " | " | " | " |
| 84 | C₂H₅ \ N— / i-C₄H₉ | " | " | " | " |

The chromogenic dye-precursor according to the present invention is a mixture comprising at least two compounds represented by the formula (I) or a mixture of a compound represented by the formula (I) and at least one compound selected from the compounds represented by the formulas (II)–(IV). Also, a mixture of at least two compounds represented by the formula (I) in which R¹ is methyl or ethyl group, R² is methyl, ethyl, isobutyl, methoxyethyl or cyclohexyl group, or R¹ and R² may join together to form

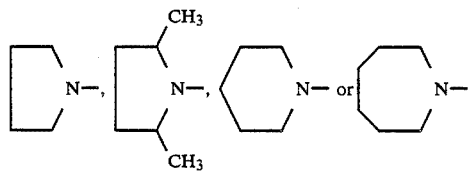

X¹ represents hydrogen atom, methyl or methoxy group, X² represents hydrogen atom, methyl, methoxy, ethoxy propoxy, isopropoxy, butoxy, isobutoxy or benzyloxy group, m is 0, 1 or 4 and n is 0, 3 or 4, m+n=4, and a mixture of the compound represented by the formula (I) in which R¹, R², X¹, X², m and n is the same as defined just above with at least one compound selected from the group consisting of a compound represented by the formula (II) in which R³ is methyl or ethyl group, R⁴ is methyl, ethyl, methoxyethyl or cyclohexyl group, or R³ or R⁴ may join together to form

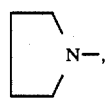

R⁵ and R⁶ are independently methyl or ethyl group, R⁷ and R⁸ are independently methyl, ethyl, propyl group or R⁷ and R⁸ may join together to form

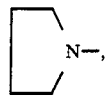

a compound represented by the formula (III) in which $R^9$ is methyl, ethyl or methoxyethyl group, $R^{10}$ is methyl, ethyl or cyclohexyl group, $R^9$ and $R^{10}$ may join together to form

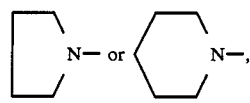

$R^{11}$ is methyl, ethyl or methoxyethyl group, $R^{12}$ is methyl or ethyl group, $R^{11}$ and $R^{12}$ may join together to form

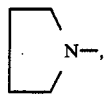

p is 0, 1, 2 or 4, q is 0, 2, 3 or 4 and p+q=4, and a compound represented by the formula (IV) in which $R^{13}$ is methyl, ethyl or butyl group, $R^{14}$ is ethyl, propyl, butyl, i-pentyl, hexyl, ethoxypropyl, cyclohexyl, methylphenyl group or

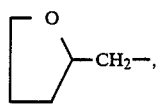

or $R^{13}$ and $R^{14}$ may join together to form

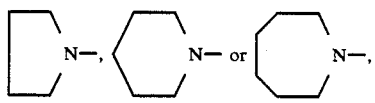

$X^3$ is hydrogen atom, chlorine atom or a methyl group, $X^4$ is hydrogen atom, chlorine atom or methyl group, and $X^5$ is hydrogen atom, chlorine atom, methyl or trifluoromethyl group, are preferred. Further, a mixture of at least two of the compounds No. 1 to No. 33 (compounds of the formula (I)), or a mixture of a compound selected from the compounds No. 1 to No. 33 with at least one selected from the group consisting of the compounds No. 34 to No. 42 (compounds of the formula (II)), the compounds No. 43 to No. 54 (compounds of the formula (III)) and the compounds No. 55 to No. 84 (compounds of the formula (IV)) are more preferred.

Furthermore, a mixture of at least two compounds of the formula (I) in which $R^1$ is methyl or ethyl group, $R^2$ is methyl or ethyl group, $R^1$ and $R^2$ may join together to form

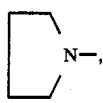

$X^1$ is hydrogen atom, methyl or methoxy group, $X^2$ is a hydrogen atom, methoxy or ethoxy group, m=4 and n=0, and a mixture of the compound(s) of the formula (I) listed above with at least one selected from the group consisting of the compound of the formula (II) in which $R^3$ is methyl or ethyl group, $R^4$ is methyl or ethyl group, $R^5$ is methyl or ethyl group, $R^6$ is methyl or ethyl group, $R^7$ is methyl, ethyl or propyl group, $R^8$ is methyl, ethyl or propyl group, the compound of the formula (III) in which $R^9$ is methyl or ethyl group, $R^{10}$ is methyl or ethyl group, $R^9$ and $R^{10}$ may join together to form

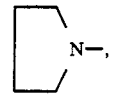

$R^{11}$ is methyl or ethyl group, $R^{12}$ is methyl or ethyl group, $R^{11}$ and $R^{12}$ may join together to form

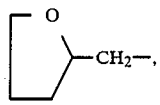

p is 0 or 4, q is 0 or 4 and p+q=4 and the compound of the formula (IV) in which $R^{13}$ is a methyl, ethyl, propyl or butyl group, $R^{14}$ is ethyl, butyl, i-pentyl, hexyl, ethoxypropyl, cyclohexyl, methylphenyl or

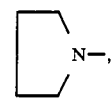

$R^{13}$ and $R^{14}$ may join together to form

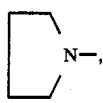

, $X^3$ is hydrogen atom or methyl group, $X^4$ is hydrogen atom, chlorine atom or methyl group and $X^5$ is hydrogen atom or methyl group are most preferred.

The content of the compound of the formula (I) in the mixture of the compound(s) of the formula (I) and at least one selected from the compounds of the formulas (II)-(IV) is not less than 10% by weight, preferably, not less than 20% by weight and, particularly preferably, not less than 30% by weight.

The compound of the formula (I) used in the present invention can be obtained by condensating 2 mol of the ethylene derivative of the following formula (V) and 1 mol of the phthalic acid derivative of the following formula (VI) under the presence of a dehydrating agent such as acetic anhydride and sulfuric acid at a temperature from 80° to 150° C.

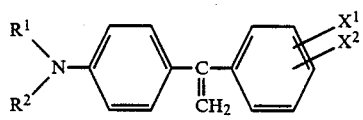  (V)

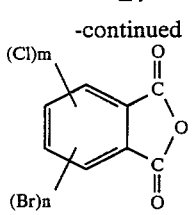

wherein $R^1$ and $R^2$ represent respectively alkyl group of 1 to 6 carbon atoms, alkyl group of 1 to 4 carbon atoms having an alkoxy group of 1 to 4 carbon atoms or cycloalkyl group of 5 to 7 carbon atoms, $X^1$ and $X^2$ represent respectively hydrogen atom, alkyl group of 1 to 8 carbon atoms, alkoxy group of 1 to 8 carbon atoms, alkoxy group of 1 to 4 carbon atoms having an alkoxy group of 1 to 4 carbon atoms, cycloalkoxy group of 5 to 7 carbon atoms, alkenyloxy group of 3 to 8 carbon atoms, benzyloxy group, substituted benzyloxy group, furfuryloxy group, tetrahydrofurfuryloxy group, phenyl group, substituted phenyl group, phenoxy group, substituted phenoxy group, fluorine atom, chlorine atom or bromine atom, m and n represent 0 or integer of 1 to 4, $m+n=4$, and $R^1$ and $R^2$ may joint together to form a heterocyclic ring.

The ethylene derivative of the formula (V) described above can be synthesized by any one of the following Grignard reactions a, b, c:

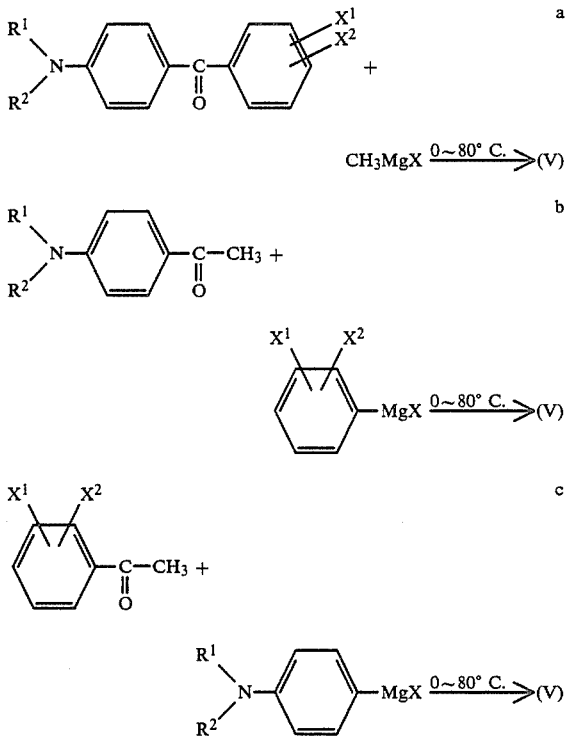

(where $R^1$, $R^2$, $X^1$, $X^2$ have the same meanings as defined above and X is halogen atom).

For preparing the heat-sensitive recording material by using the chromogenic dye-precursor according to the present invention, known methods described, for example, in Japanese patent publication No. 45-14039 (1970) (corresponding to U.S. Pat. No. 3,539,375), Japanese patent laying-open (KOKAI) No. 59-33186 (1984), etc. can be adopted. Further, the chromogenic dye-precursor may be mixed by previously dissolving or melting them, or mixing crystals thereof before or after the pulverization.

Further, other chromogenic dye-prescursor which can assume various colors other than those of the substance derived from the compound of the formulas (I)–(IV) may be mixed in order to attain more complete color hue, coloring sensitivity, coloring density, etc.

For instance,
3,3-bis(aminophenyl)-6-aminophthalide,
3,3-bis(indolyl)phthalide, 3-aminofluoran, aminobenzofluoran,
spiropyran, phenoxazine, leuco auramine, carbazolylmethane,
3-indolyl-3-(amino)phenylphthalide and
3-indolyl-3-(aminophenyl)azaphthalide can be used.

As a binder for preparing the heat-sensitive recording material, polyvinyl alcohol, methylcellulose, hydroxy ethylcellulose, carboxymethylcellulose, gum arabic, gelatin, starch, polyvinyl pyrrolidone, styrene-maleic anhydride copolymer and the like can be used. As the developer, clay, bentonite, active white clay, zinc chloride, zinc salt of salicylic acid derivative, p-phenylphenol formalin resin, p-octylphenyl formalin resin and zinc salt thereof, methyl 4-hydroxybenzoate, benzyl 4-hydroxybenzoate, bisphenol A, 4,4'-thiodiphenol, bis-(4-hydroxy-3-methylphenyl)sulfide,
4,4'-dihydroxydiphenyl sulfone,
4-hydroxy-4'-methyldiphenyl sulfone,
4-hydroxy-4'-propoxydiphenyl sulfone,
4,4'-dihydroxy-3,3'-diallyldiphenyl sulfone,
1,5-di(4-hydroxyphenylthio)-3-oxapentane,
1,7-di(4-hydroxyphenylthio)-3,5-dioxaheptane,
1,8-di(4-hydroxyphenylthio)-3,6-dioxaoctane,
bis(4-hydroxy-3-methylphenyl)sulfide,
dimethyl hydroxyphthalate and
2,4-dihydroxybenzophenone can be used.

As the sensitizer, urea, phthalic anhydride, acetanilide, paraffin wax, carnauba wax, higher fatty acid, higher fatty acid ester, higher fatty acid amide, phthalic acid ester, terephthalic acid ester, benzyl 4-benzyloxybenzoate, naphthol benzyl ether, 1,4-dialkoxynaphthalene, m-terpheyl,
p-benzylbiphenyl, dibenzylbenzene,
1-hydroxy-2-naphthoic acid ester,
2-hydroxy-3-naphthoic acid ester,
4,4'-dialkoxydiphenyl sulfone, benzamide, diphenylamine, benzenesulfonamide, benzenesulfonanilide, carbazole and hydroquinone benzyl ether can be mixed therewith.

Further, addition of various antioxidants, anti-aging agents and UV absorbers, or overcoat with polymeric material for the heat-sensitive recording material is effective for the improvement in the light fastness and the storage stability of the colored images.

The heat-sensitive recording material according to the present invention can provide the black colored images having been increasingly demanded, which shows absorption at near infrared region as well as excellent performances in moisture resistance, resistance to plasticizer, oil resistance, light fastness and the like and, accordingly, it is of high industrial value as heat-sensitive recording paper for OCR or the like.

This invention will now be described more specifically referring to the following non-limitative examples.

EXAMPLE 1

| (1) Preparation of Chromogenic Dye-precursor Dispersion (Liquid A) | |
| --- | --- |
| 3,3-bis[2-(p-dimethylaminophenyl)-2-(p-methoxyphenyl)ethenyl]-4,5,6,7-tetrachlorophthalide (Compound No. 3) | 3 parts |
| 3,3-bis[2-(p-pyrrolidinophenyl)-2-(p-methoxyphenyl)ethenyl]-4,5,6,7-tetrachlorophthalide (Compound No. 11) | 3 parts |
| Kaolin | 15 parts |
| Aqueous 10% polyvinyl alcohol solution | 100 parts |
| Water | 85 parts |

The mixture was pulverized by using a paint shaker (manufactured by Toyo Seiki Co.) till the average particle diameter of the chromogenic dye-precursor was to 2 μm.

| (2) Preparation of Developer Dispersion (Liquid B) | |
| --- | --- |
| Bisphenol A | 15 parts |
| Zinc stearate | 10 parts |
| Aqueous 10% polyvinyl alcohol solution | 100 parts |

The mixture was pulverized by a paint shaper till the average particle diameter was to 3 μm.

(3) Preparation and Coating of Heat Sensitive Coating Liquid 10 parts of the liquid A and 6.5 parts of the liquid B were mixed and stirred to obtain a heat-sensitive coating liquid. The coating liquid was uniformly coated on a paper sheet so as to obtain a paper having a 6 g/m² of the coated material in dry weight by using a wire bar, followed by drying to obtain heat-sensitive recording paper. The heat-sensitive recording paper was colorless, free from background fogging and colored densely black rapidly by heating with a thermopen or the like. The developed color image was excellent in the light fastness and the moisture resistance and since it had an intense absorption in 700–1000 nm, OCR reading was possible. Further, the coated surface was also excellent in the light fastness and not pigmented under sunlight irradiation.

EXAMPLES 2–21

Heat-sensitive recording paper sheets were obtained by the same procedures as in Example 1 except mixing the chromogenic dye-precursors shown in Table 1 instead of 3 parts of the compound No. 3 and the compound No. 11.

These heat-sensitive recording paper sheets had excellent performance like that in Example 1.

COMPARATIVE EXAMPLE 1

Heat-sensitive recording paper sheet was obtained in the same procedures as in Example 1 except using 6 parts of the No. 3 compound as the chromogenic dye-precursor.

COMPARATIVE EXAMPLES 2–13

Heat-sensitive recording paper sheets were obtained by the same procedures as in Example 1 except using the compounds shown in Table 2 as the chromogenic dye-precursor.

(TEST)

The moisture resistance and the resistance to plasticizer were tested by the following methods for the heat-sensitive recording paper sheets obtained in the Examples and the Comparative Examples. The results are shown in Table 1 and Table 2.

(1) Moisture Resistance Test

Respective heat-sensitive paper sheets were evenly colored by using a heat-sensitive coloring tester (manufactured by Matsushita Denshi Buhin Co.) with an application voltage at 15 volt and a pulse width of 2.5 m sec. After leaving the colored images for 4 days in an atmosphere at a temperature of 40° C. and a relative humidity of 90%, the light absorption at 900 nm was measured by using a spectrophotometer (Model UV 365, manufactured by Shimazu Seisakusho, Co.). Then, the image residual rate was determined by the following equation to define it as the moisture resistance:

$$\text{Moisture Resistance (\%)} = \frac{\text{light absorption after 4 days at 40° C.-90\%RH}}{\text{initial light absorption}} \times 100$$

The specimens of Comparative Example 8, 9, 10 composed only of the compound of the general formula (IV) were measured at 600 nm (laso in the plasticizer-resistance test).

(2) Plastizer-resistance test

The image area colored under the same conditions as on (1) above was covered with a soft vinyl chloride sheet (Kuke-64, manufactured by Kokuyo Co.) and placed in a thermostat at 60° C. for 3 hours under the load of 4 g/cm². The light absorption at 900 nm was measured in the same manner as in (1) and the image residual ratio was determined by the following equation to define it as the plasticizer-resistance:

$$\text{Plasticizer-resistance (\%)} = \frac{\text{light absorption after 60° C.-3 hr}}{\text{initial light absorption}} \times 100$$

TABLE 1

| Example No. | Amount of chromogenic dye-precursor mixed | | Moisture Resistance (%) | Plasticizer resistance (%) |
| --- | --- | --- | --- | --- |
| | Compound of the general formula (I) | Compound of the general formula (II), (III), (IV) | | |
| 1 | No. 3 (3 parts) No. 11 (3 parts) | | 68 | 89 |
| 2 | No. 3 (4 parts) No. 11 (2 parts) | | 59 | 88 |
| 3 | No. 3 (2 parts) No. 11 (4 parts) | | 73 | 88 |
| 4 | No. 3 (3 parts) No. 15 (3 parts) | | 60 | 79 |
| 5 | No. 11 (3 parts) | No.34 (3 part) | 86 | 88 |
| 6 | No. 3 (3 parts) | No.34 (3 part) | 80 | 81 |
| 7 | No. 3 (3 parts) | No.43 (3 part) | 85 | 98 |
| 8 | No. 3 (3 parts) | No.61 (3 part) | 70 | 85 |
| 9 | No. 3 (3 parts) | No.71 (3 part) | 82 | 86 |
| 10 | No. 3 (3 parts) | No.59 (3 part) | 73 | 91 |
| 11 | No. 3 (3 parts) | No.65 (3 part) | 82 | 86 |
| 12 | No. 3 (4 parts) | No.65 (2 part) | 80 | 83 |
| 13 | No. 3 (3 parts) | No.60 (3 part) | 84 | 86 |
| 14 | No. 3 (4 parts) | No.60 (2 part) | 81 | 82 |
| 15 | No. 3 (4.5 parts) | No.60 (1.5 part) | 75 | 78 |
| 16 | No. 3 (2 parts) No. 10 (2 parts) No. 11 (2 parts) | | 70 | 80 |
| 17 | No. 3 (2 parts) No. 11 (2 parts) | No.43 (2 part) | 90 | 95 |
| 18 | No. 3 (2 parts) | No.65 (2 part) | 76 | 96 |

TABLE 1-continued

| Example No. | Amount of chromogenic dye-precursor mixed | | Moisture Resistance (%) | Plasticizer resistance (%) |
|---|---|---|---|---|
| | Compound of the general formula (I) | Compound of the general formula (II), (III), (IV) | | |
| 19 | No. 11 (2 parts) No. 3 (2 parts) | No.34 (2 part) No.60 (2 part) | 85 | 85 |
| 20 | No. 3 (2 parts) | No.34 (2 part) No.43 (2 part) | 87 | 88 |
| 21 | No. 3 (2 parts) No. 11 (2 parts) | No.60 (1 part) No.65 (1 part) | 86 | 87 |

TABLE 2

| Comparative Example No. | Chromogenic dye-precursor | Moisture resistance (%) | Plasticizer-resistance (%) |
|---|---|---|---|
| 1 | No. 3 (6 parts) | 33 | 70 |
| 2 | No. 10 (6 parts) | 63 | 70 |
| 3 | No. 11 (6 parts) | 80 | 83 |
| 4 | No. 15 (6 parts) | 63 | 84 |
| 5 | No. 34 (6 parts) | 81 | 92 |
| 6 | No. 36 (6 parts) | 71 | 84 |
| 7 | No. 43 (6 parts) | 89 | 98 |
| 8 | No. 59 (6 parts) | 86 | 95 |
| 9 | No. 60 (6 parts) | 94 | 91 |
| 10 | No. 65 (6 parts) | 93 | 92 |
| 11 | No. 43 (3 parts) No. 34 (3 parts) | 86 | 95 |
| 12 | No. 34 (3 parts) No. 36 (3 parts) | 77 | 88 |
| 13 | No. 34 (3 parts) No. 65 (3 parts) | 59 | 62 |

From the test, it was confirmed that the heat-sensitive recording paper according to the present invention is excellent in the moisture resistance and the resistance to plasticizer.

What is claimed is:

1. A heat-sensitive recording material comprising a substrate on which there is applied:
   (1) an effective amount of:
      (i) a chromogenic dye-precursor selected from the group consisting of a mixture of at least two divinyl phthalide compounds represented by the formula (I);
      (ii) a mixture of a divinyl phthalide compound represented by the formula (I) and a compound represented by the formula (II);
      (iii) a mixture of a divinyl phthalide compound represented by the formula (I) and a compound represented by the formula (III);
      (iv) a mixture of adivinyl phthalide compound represented by the formula (I) a compound represented by the formula (IV);
      (v) a mixture of a divinyl phthalide compound represented by the formula (I), a compound represented by the formula (II) and a compound represented by the formula (III);
      (vi) a mixture of a divinyl phthalide compound represented by the formula (I), a compound represented by the formula (II) and a compound represented by the formula (IV); and
      (vii) a mixture of a divinyl phthalide compound represented by the formula (I) and at least two compounds represented by the formula (IV); wherein said divinyl phthalide compounds represented by the formula (I) are as follows:

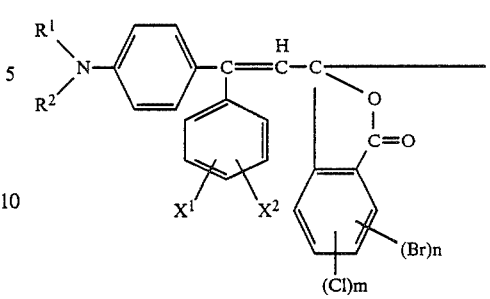

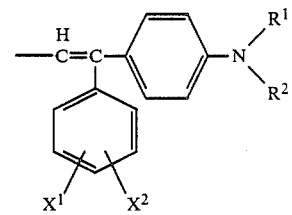

wherein, $R^1$ and $R^2$ represent respectively an alkyl group of 1 to 6 carbon atoms, an alkyl group of 1 to 4 carbon atoms having an alkoxy group of 1 to 4 carbon atoms or a cycloalkyl group of 5 to 7 carbon atoms; $X^1$ and $X^2$ represent respectively a hydrogen atom, an alkyl group of 1 to 8 carbon atoms, an alkoxy group of 1 to 8 carbon atoms, an alkoxy-alkoxy group wherein each alkoxy subgroup is of 1 to 4 carbon atoms, a cycloalkoxy group of 5 to 7 carbon atoms, an alkenyloxy group of 3 to 8 carbon atoms, a benzyloxy group, a substituted benzyloxy group, a furfuryloxy group, a tetrahydrofurfuryloxy group, a phenyl group, a substituted phenyl group, a phenoxy group, a substituted phenoxy group, a fluorine atom, a chlorine atom or bromine atom; m and n represent 0 or an integer of 1 to 4; m+n=4, and $R^1$ and $R^2$ may join together to form a heterocyclic ring, and wherein each of said compounds represented by the formulas (II), (III) and (IV) are as follows:

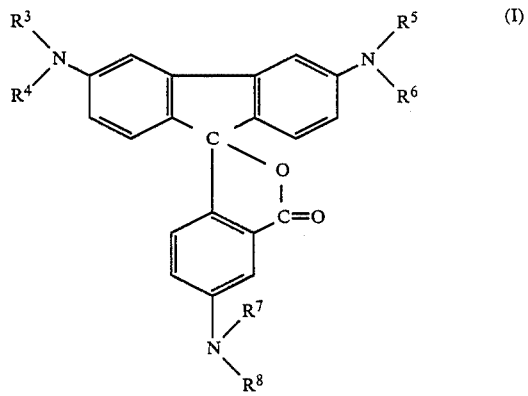

-continued

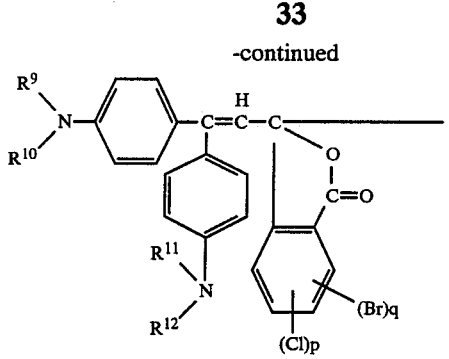  (III)

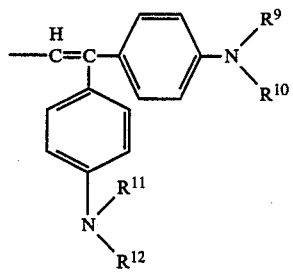

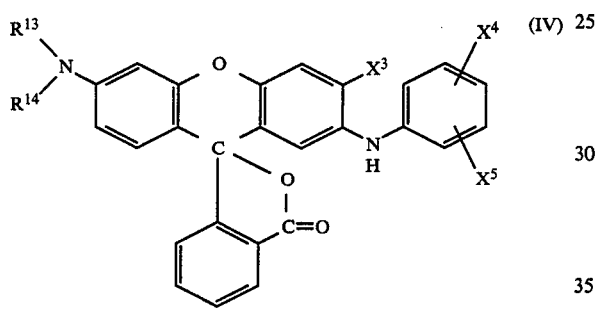  (IV)

where, $R^3$–$R^{14}$ represent an alkyl group of 1 to 6 carbon atoms, an alkyl group of 1 to 4 carbon atoms each having an alkoxy group of 1 to 4 carbon atoms, a cycloalkyl group of 5 to 7 carbon atoms, a phenyl group, a substituted phenyl group or tetrahydrofurfuryl group; p and q represent 0 or an integer of 1 to 4; p+q=4; $X^3$ represents a hydrogen atom, an alkyl group of 1 to 4 carbon atoms or a chlorine atom; $X^4$ and $X^5$ respectively represent a hydrogen atom, a chlorine atom or trifluromethyl group; and wherein $R^3$ and $R^4$, $R^6$, $R^7$ and $R^8$, $R^9$ and $R^{10}$, $R^{11}$ and $R^{12}$, and $R^{13}$ and $R^{14}$ may join together to form heterocyclic rings,
and wherein said heat-sensitive recording material further comprises
(2) a developer, and
(3) a binder.

2. A heat-sensitive recording material as defined in claim 1, wherein said chromogenic dye-precursor is a mixture selected from mixtures of (a) a compound of said formula (I) and a compound of said formula (IV), (b) a compound of said formula (I), a compound of said formula (II) and a compound of said formula (IV), and (c) a compound of said formula (I) and two different compounds of said formula (IV).

3. A heat-sensitive recording material as defined in claim 1, wherein said chromogenic dye-precursor is a mixture selected from mixtures of (a) a compound of said formula (I) and a compound of said formula (IV), and (b) a compound of said formula (I) and two different compounds of said formula (IV).

4. A heat-sensitive recording material as defined in claim 1, wherein the divinyl phthalide compound is a compound in which $R^1$ represents methyl or ethyl group, $R^2$ represents methyl, ethyl, isobutyl, methoxyethyl or cyclohexyl group, or $R^1$ and $R^2$ may join together to form

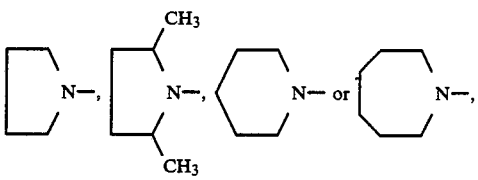

$X^1$ represents hydrogen atom, methyl or methoxy group, $X^2$ represents hydrogen atom, methyl, methoxy or ethoxy group, m is 0, 1 or 4, n is 0, 3 or 4, and m+n=4 in the formula (I),
the compound represented by the formula (II) is one in which $R^3$ represents methyl or ethyl group, $R^4$ methyl, ethyl, methoxyethyl or cyclohexyl group or $R^3$ and $R^4$ may join together to form

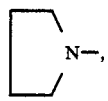

$R^5$ and $R^6$ represent independently methyl or ethyl group, $R^7$ and $R^8$ represent independently methyl, ethyl or propyl group or $R^7$ and $R^8$ may join together to form

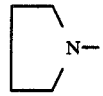

in the formula (II),
the compound represented by the formula (III) is one in which $R^9$ represents methyl, ethyl or methoxyethyl group, $R^{10}$ represents methyl, ethyl or cyclohexyl group, $R^9$ and $R^{10}$ may join together to form

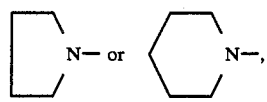

$R^{11}$ represents methyl, ethyl or methoxyethyl group, $R^{12}$ represents methyl or ethyl, $R^{11}$ and $R^{12}$ may join together to form

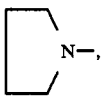

p is 0, 1, 2 or 4, q is 0, 2, 3 or 4, p+q=4 in the formula (III), and
the compound represented by the formula (IV) is one in which $R^{13}$ represents methyl, ethyl or butyl group, $R^{14}$ represents ethyl, propyl, butyl, i-pentyl, hexyl, ethoxypropyl, cyclohexyl, methylphenyl or

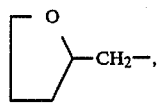

or $R^{13}$ and $R^{14}$ may join together to form

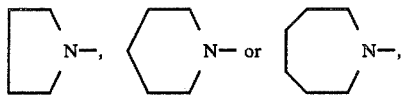

$X^3$ represents hydrogen atom, chlorine atom or methyl group, $X^4$ represents hydrogen atom, chlorine atom or methyl group and $X^5$ represents hydrogen atom, chlorine, methyl group and trifluoromethyl group in the formula (IV).

5. A heat-sensitive recording material as defined in claim 4, wherein the divinyl phthalide compound is a compound in which $R^1$ represents methyl or ethyl group, $R^2$ represents methyl or ethyl group, or $R^1$ and $R^2$ may join together to form

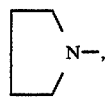

$X^1$ represents hydrogen atom, methyl or methoxy group, $X^2$ represents hydrogen atom, methoxy or ethoxy group, $m=4$ and $n=0$ in the formula (I), the compound represented by the formula (II) is one in which $R^3$ represents methyl or ethyl group, $R^4$ represents methyl or ethyl group, $R^5$ represents methyl or ethyl group, $R^6$ represents methyl or ethyl group, $R^7$ represents methyl, ethyl or propyl group, $R^8$ represents methyl, ethyl or propyl group in the formula (II), the compound represented by the formula (III) is one in which $R^9$ represents methyl or ethyl group, $R^{10}$ represents methyl or ethyl group, $R^9$ and $R^{10}$ may join together to form

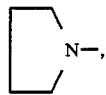

$R^{11}$ represents methyl or ethyl group, $R^{12}$ represents methyl or ethyl group, $R^{11}$ and $R^{12}$ may join together to form

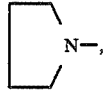

p is 0 or 4, q is 0 or 4 and $p+q=4$ in the formula (III), and the compound represented by the formula (IV) is one in which $R^{13}$ represents methyl, ethyl or butyl group, $R^{14}$ represents ethyl, propyl, butyl, i-pentyl, hexyl, ethoxypropyl, cyclohexyl, methylphenyl group or

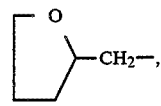

$R^{13}$ and $R^{14}$ may join together to form

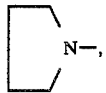

$X^3$ represents hydrogen atom or methyl group, $X^4$ represents hydrogen atom, chlorine atom or methyl group and $X^5$ represents hydrogen atom or methyl group in the formula (IV).

6. A heat-sensitive recording material as defined in claim 1, wherein the content of the compound represented by the formula (I) in the chromogenic dye-precursor mixture is not less than 20% by weight.

7. A heat-sensitive recording material as defined in claim 6, wherein the content of the compound represented by the formula (I) in the chromogenic dye-precursor mixture is not less than 30% by weight.

* * * * *